United States Patent [19]
Bacich et al.

[11] Patent Number: 5,389,100
[45] Date of Patent: Feb. 14, 1995

[54] CONTROLLER FOR MANIPULATION OF INSTRUMENTS WITHIN A CATHETER

[75] Inventors: Steven R. Bacich, Lagna Niguel; Gary Woker, Escondido; Guy R. Lowery, Mission Viejo; Fred R. Tietge, San Diego, all of Calif.

[73] Assignee: Imagyn Medical, Inc., Laguna Niguel, Calif.

[21] Appl. No.: 788,338

[22] Filed: Nov. 6, 1991

[51] Int. Cl.$^6$ .................................... A61M 37/00
[52] U.S. Cl. .................................... 606/108; 604/95; 604/159; 604/164; 604/271; 604/280; 604/283
[58] Field of Search ............... 606/1, 108; 128/4, 10, 128/772; 604/95, 156, 271, 280, 283, 158, 159, 164, 171, 271, 264, 159

[56] References Cited

U.S. PATENT DOCUMENTS

| | | | |
|---|---|---|---|
| 1,087,845 | 2/1914 | Stevens | 604/159 |
| 1,901,731 | 3/1933 | Buerger . | |
| 3,552,384 | 1/1971 | Pierie et al. . | |
| 3,835,854 | 9/1974 | Jewett . | |
| 4,027,510 | 6/1977 | Hiltebrandt . | |
| 4,178,920 | 12/1979 | Cawood, Jr. et al. . | |
| 4,243,040 | 1/1981 | Beecher | 604/271 |
| 4,383,532 | 5/1983 | Dickhudt . | |
| 4,397,091 | 8/1983 | Gustavsson et al. | 604/159 X |
| 4,421,106 | 12/1983 | Uehara . | |
| 4,530,698 | 7/1985 | Goldstein et al. | 604/271 |
| 4,606,347 | 8/1986 | Fogarty et al. . | |
| 4,607,620 | 8/1986 | Storz . | |
| 4,616,648 | 10/1986 | Simpson | 604/159 |
| 4,641,634 | 2/1987 | Storz . | |
| 4,656,999 | 4/1987 | Storz . | |
| 4,791,913 | 12/1988 | Maloney . | |
| 4,846,785 | 7/1989 | Cassou et al. . | |
| 4,946,440 | 8/1990 | Hall | 604/95 |
| 5,064,415 | 11/1991 | Walder et al. | 604/171 X |
| 5,100,383 | 3/1992 | Lichtenstein | 604/271 |
| 5,163,927 | 11/1992 | Woker et al. | 604/271 |

FOREIGN PATENT DOCUMENTS

| | | | |
|---|---|---|---|
| 0450345 | 3/1913 | France | 604/159 |
| 2406823 | 8/1975 | Germany | 604/271 |

OTHER PUBLICATIONS

"The Ins And Outs of Toposcopy and The Everting Catheter", D. R. Shook, SOMA, pp. 22–27, Jul. 1987.

Primary Examiner—Stephen C. Pellegrino
Assistant Examiner—Jeffrey A. Schmidt
Attorney, Agent, or Firm—Gordon L. Peterson

[57] ABSTRACT

An everting catheter system which includes an elongated outer catheter having an outer catheter lumen and an opening, an elongated inner catheter movable in the outer catheter lumen and having the inner catheter lumen adapted to receive an elongated instrument and an everting element coupled to the outer catheter and the inner catheter. With movement of the inner catheter in the outer catheter lumen, the everting element can be everted through the opening of the outer catheter. A controller is coupled to the inner catheter for moving the inner catheter in the outer catheter lumen and for moving the instrument in the inner catheter lumen.

24 Claims, 4 Drawing Sheets

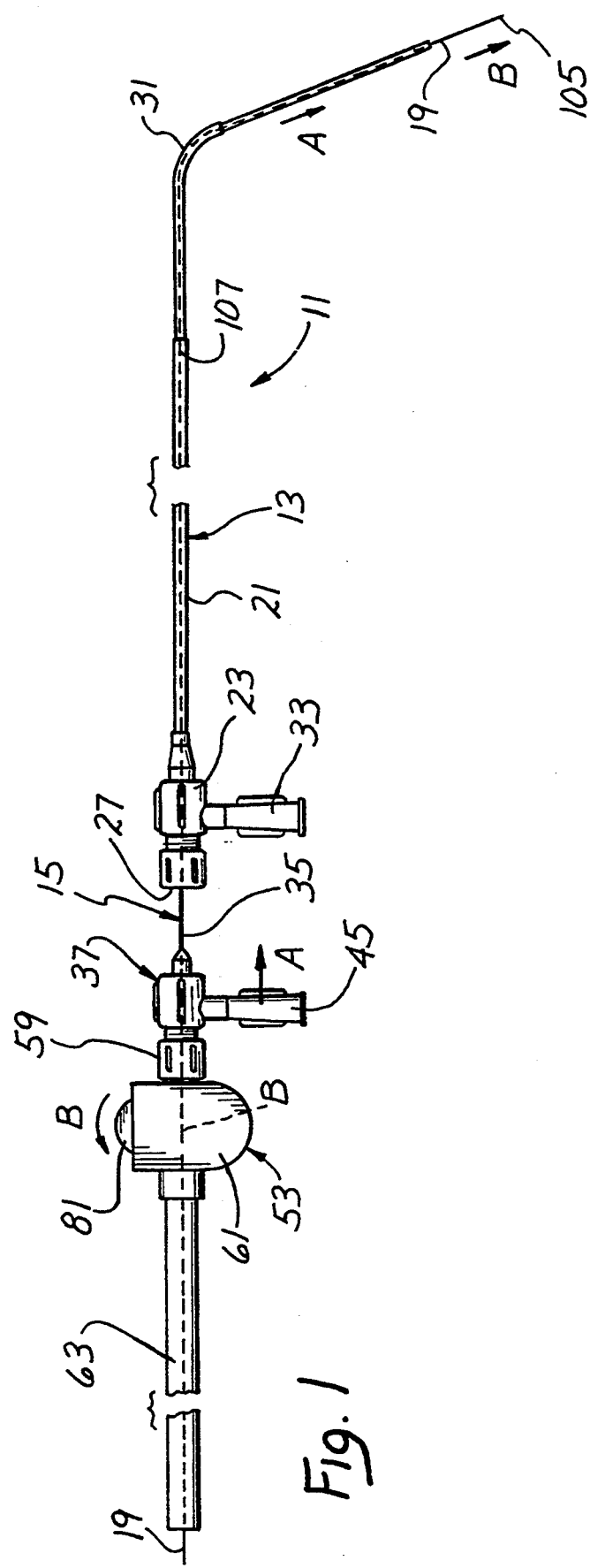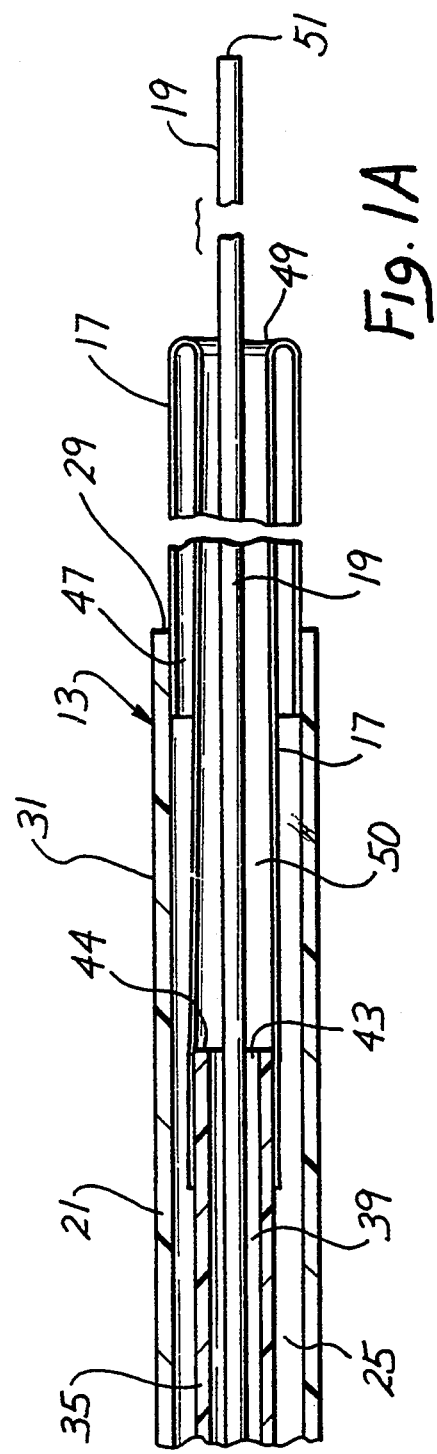

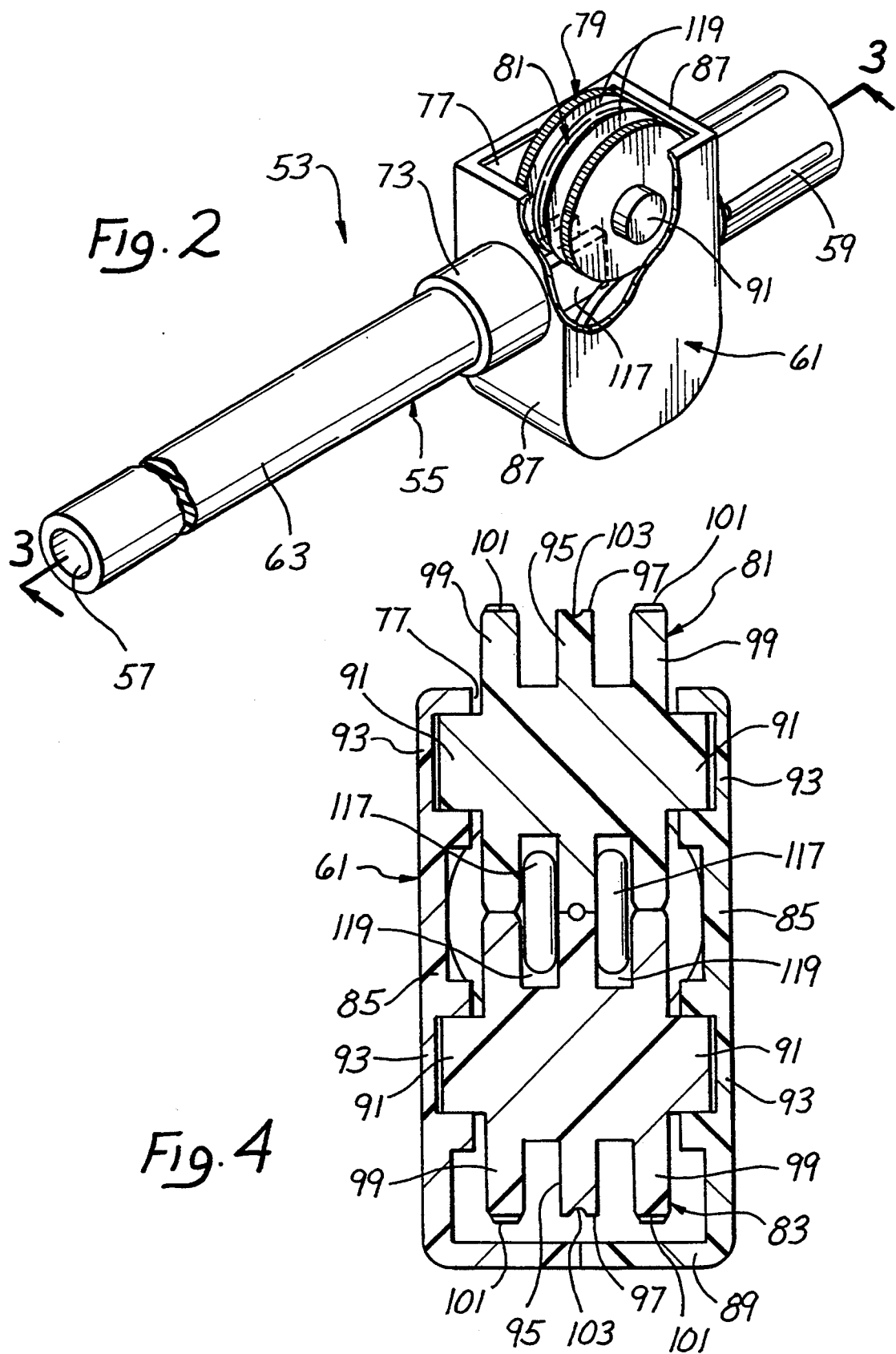

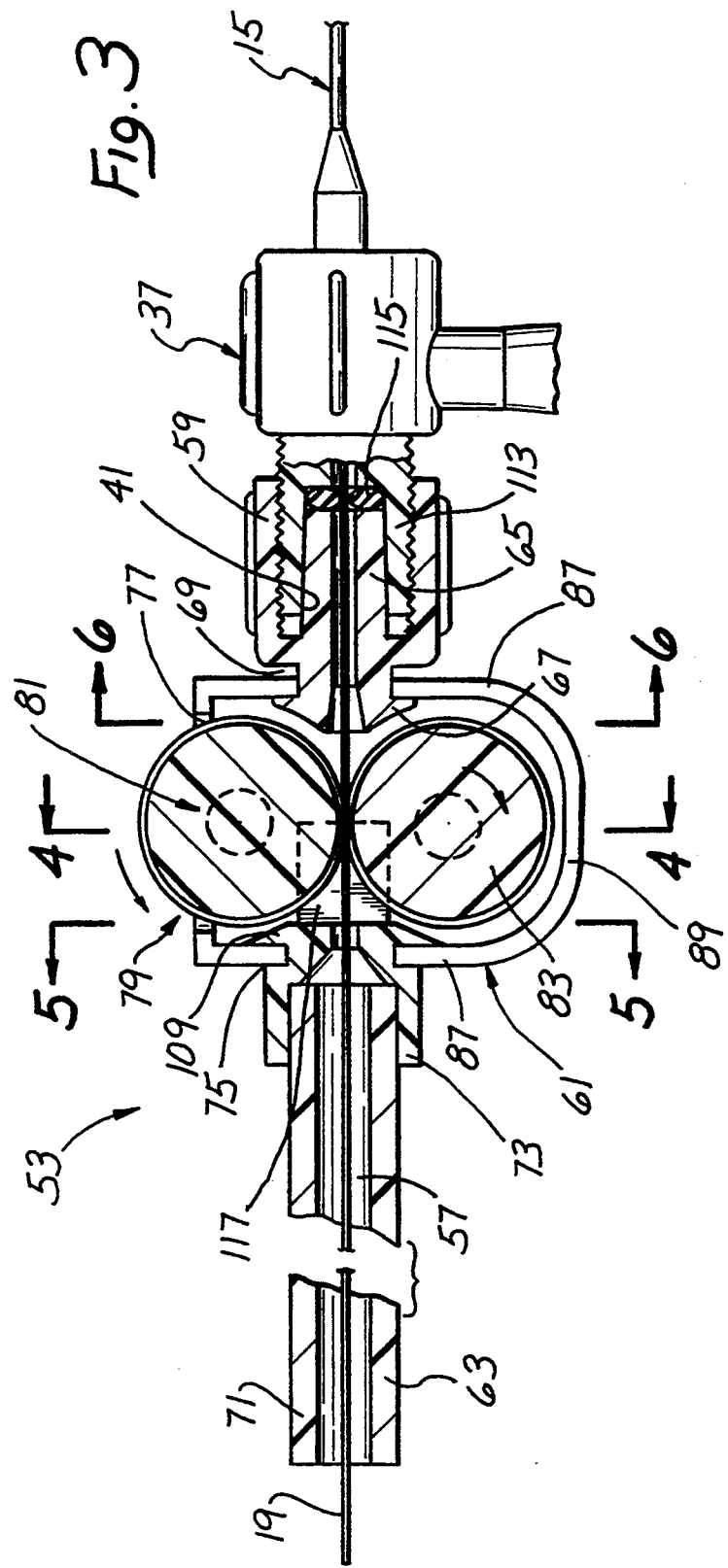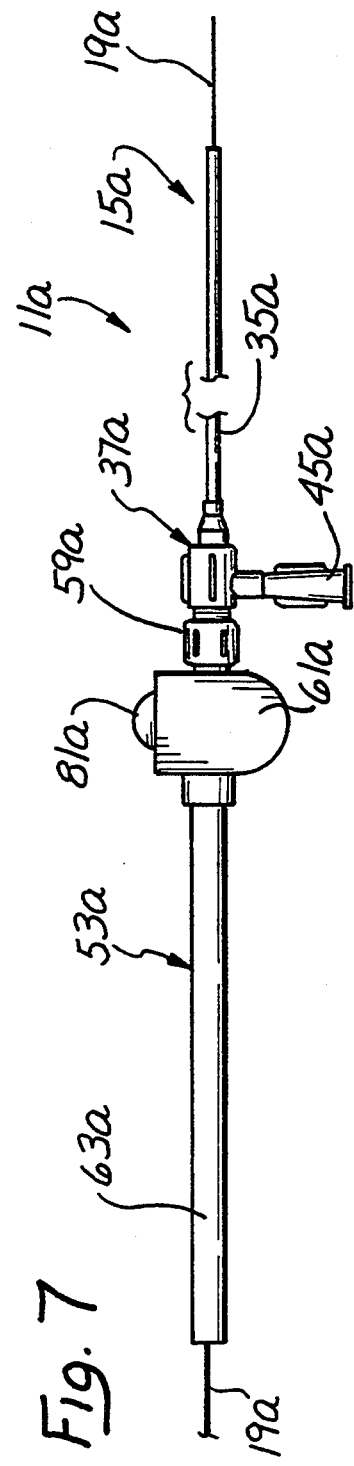

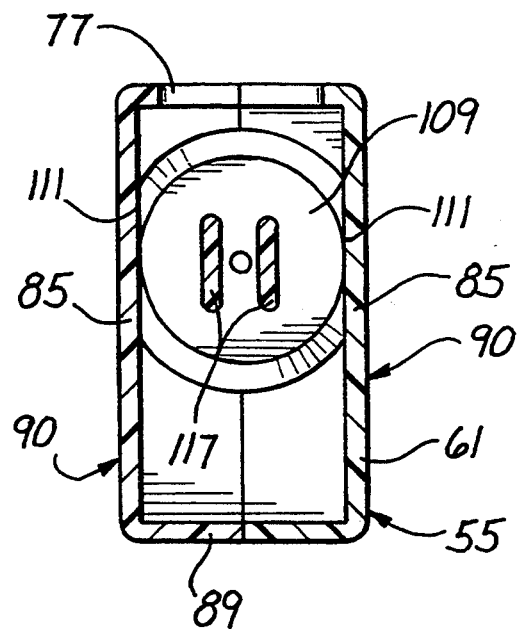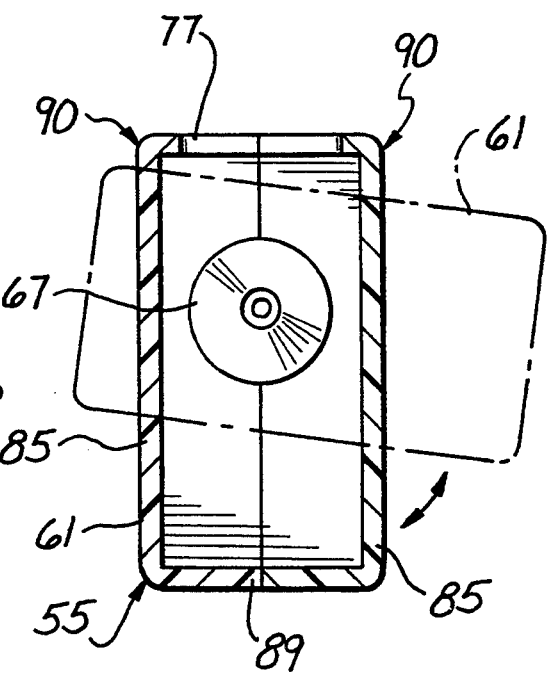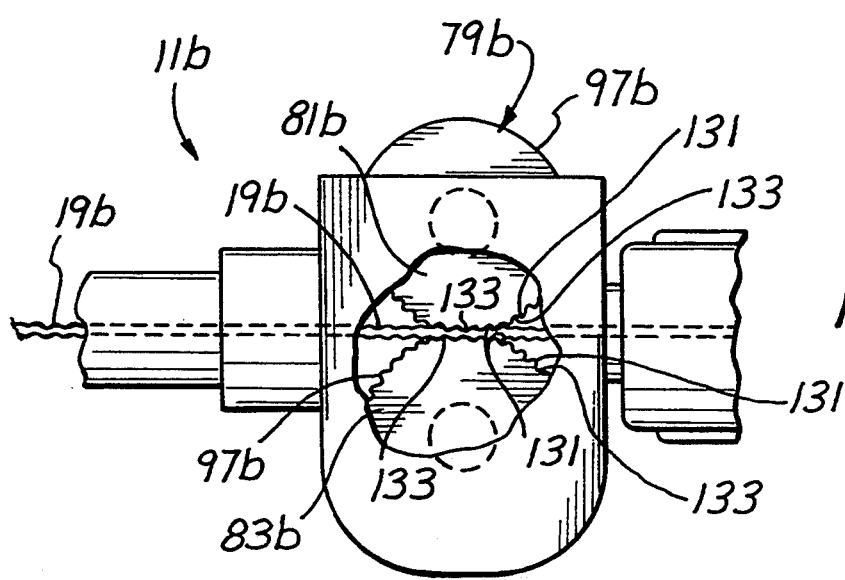

CONTROLLER FOR MANIPULATION OF INSTRUMENTS WITHIN A CATHETER

BACKGROUND OF THE INVENTION

An everting catheter typically includes an outer catheter having an outer catheter lumen and an inner catheter movable longitudinally in the outer catheter lumen and having an inner catheter lumen. An everting element is coupled to the outer catheter and the inner catheter so that, with movement of the inner catheter distally in the outer catheter lumen, the everting element can be everted through an opening in the outer catheter.

An everting catheter of this type can be inserted through a passage in the human body with the everting element in an inverted position. An elongated, flexible instrument can then be introduced through the inner catheter lumen and the everting element to position the instrument into a desired body region and accomplish any of a variety of medical procedures and/or viewing of internal body regions.

The use of an everting catheter requires the control and manipulation of several different components. For example, movement and control of the inner catheter is required in connection with the eversion and inversion of the everting element, and movement and control of the instrument relative to the inner catheter is necessary in order to properly position the instrument within the body of the patient. In addition, the outer catheter must be properly positioned. Because of these multiple controlling and positioning tasks, the use of an everting catheter system commonly requires two attendants.

Non-everting catheters also may require multiple controlling and positioning functions during use. For example, a non-everting catheter may have an instrument extending through the lumen of the catheter and into the body of the patient. During use, it is commonly necessary to position the catheter and the instrument within the patient; however, unlike everting catheters, only a single catheter needs to be positioned.

Various controllers for manipulating an instrument in a catheter lumen are known. For example, one prior art device, known as a guidewire torquer, includes a collet clamped onto a guidewire which extends through an access catheter or angioplasty catheter. The torquer allows the operator to operate the guidewire about a central axis and move the guidewire proximally and distally. However, the torquer does not control the position of the catheter.

In the field of arthrectomy devices, it is known to use a hand-held controller attached to a guiding catheter. The controller rotates a drive cable or instrument shaft which manipulates cutting surfaces on the distal end of the instrument. The controller has a pull knob which can advance and withdraw the cutting surface of the instrument within the lumen of the catheter. Other controllers of this type rotate an instrument or drive cable which imparts rotational energy to the cutting surface.

Another known controller imparts ultrasonic energy to an instrument shaft which extends through the lumen of a catheter. A controller of this type may also have a pistol-trigger grip which allows an ultrasonic ablative surface to be advanced and withdrawn. Other types of pistol-trigger grip devices which are attached to primary catheters can be used for grabbing forceps or scissors.

SUMMARY OF THE INVENTION

This invention provides a controller which greatly simplifies catheter and instrument positioning and control within the body of a patient. Although the invention is particularly adapted for use with an everting catheter where positioning and control functions are more complex, this invention is also adapted for use with a non-everting catheter.

With respect to the everting catheter, this invention provides an everting catheter system which includes an everting catheter and a controller. The controller is coupled to the inner catheter for moving the inner catheter in the outer catheter lumen and for moving the instrument in the inner catheter lumen relative to the inner catheter. Because the controller is coupled to the inner catheter, it can move and position the inner catheter. In addition, the controller has the capability of moving and positioning the instrument in the inner catheter lumen. The controller enables one-handed control and positioning of both the inner catheter and the instrument leaving the other hand of the attendant free. This converts what has characteristically been a two-attendant operation to a one-attendant operation.

The movement of the instrument in the inner catheter lumen may be longitudinal and/or rotational. In order to accomplish this movement, the controller preferably includes a driving device for moving the instrument.

The driving device may take many different forms and, in a preferred construction, includes a movable, endless member for contacting and driving the instrument longitudinally in the inner catheter lumen. For example, the movable, endless member may be a drive wheel, drive belt, drive chain or other endless member. One advantage of an endless, movable member is that no shuttle or back and forth movement is necessary for it to move the instrument through substantial distances. In addition, it promotes compactness and simplicity of the controller.

In a preferred construction, the driving device also includes a secondary wheel engageable with the instrument and cooperable with the drive wheel for moving the instrument. An important advantage of the secondary wheel is that it cooperates with the driving wheel to provide rolling, as opposed to sliding, contact with the instrument. The secondary wheel may also be a drive wheel or it may be an idler wheel which is driven solely by virtue of its contact with the instrument.

The driving device may be driven manually or with a motor. A manual drive has the advantage of light weight, lower cost and retention of "feel" by the operator. Again, to avoid a shuttling or ratcheting type of operation, it is preferred to use an endless, movable member having a region engageable by a thumb of an operator to impart a manual driving force to the driving device for moving the instrument longitudinally. This latter endless, movable member may be the same endless movable member which contacts and drives the instrument or it may be a separate member contacted by the thumb which drives the endless, movable member directly or through intermediate drive wheels or the like.

In a preferred construction, the controller is also able to rotate the instrument. At least a portion of the controller, and preferably the driving device, may be movable or rotatable to accomplish this function.

The controller preferably includes a supporting structure which in turn may include a housing coupled to a proximal end portion of the inner catheter. The housing may be a separate member permanently or releasably coupled to the proximal end portion of the inner catheter. Alternatively, the housing and inner catheter may be of one-piece construction, in which event, the coupling of the housing to the catheter is an integral coupling. In any event, the housing has a passage which communicates with the inner catheter lumen and which is adapted to receive the instrument.

Although the housing can be of various different constructions, it preferably forms a handle section or handle which is adapted to be manually grasped. In a preferred construction, the housing extends proximally of the region of the endless, movable member, which is engageable and drivable by the thumb of an operator, to form the handle. By placing the handle proximally of the thumb-driven region of the member, driving of such member by the thumb of an operator in a one-handed operation is facilitated.

The housing can advantageously be used to provide for rotation of the instrument. With this construction, the housing includes a rotatable section or drive section rotatable generally about the axis of the passage, and the driving device is carried by the rotatable section, and is capable of gripping the instrument. Accordingly, rotation of the rotatable section rotates the instrument.

In one embodiment, the housing is a separate member which is coupled to the proximal end portion of the catheter. To accomplish this, the housing of the controller can advantageously include a mounting section adapted to be coupled to the catheter. In this event, the drive section of the housing is coupled to both the handle and the mounting section intermediate the handle and the mounting section.

When the driving device includes both a drive wheel and a secondary wheel, the peripheral surfaces of these wheels are arranged in generally confronting relationship and adapted to receive the instrument therebetween. At least one of these peripheral surfaces of the wheels may have a groove for receiving the instrument. The groove is particularly advantageous for an instrument, such as certain endoscopes, having a relatively fragile lens and/or optical system near the distal end portion of the instrument and a cross section which reduces toward the distal end. Instruments of this type can be slid through this groove without damaging the optical system, and the thicker, more proximal regions of the instrument can still be gripped with sufficient firmness by the wheels to form a driving connection between the wheels and the instrument.

In a preferred construction, at least a portion of the passage through the controller extends proximally of the drive wheel and the secondary wheel. In this event, the controller preferably includes means in the passage for guiding the instrument from the proximal portion of the passage to the driving device. Although this means may include any form of constraint on the instrument which will achieve the desired guiding purpose, in a preferred embodiment, the guiding means includes first and second spaced alignment tabs for guiding the instrument between the drive wheel and the secondary wheel. In order to permit the tabs to extend all the way to the region between the drive wheel and the secondary wheel, the wheels preferably define first and second annular spaces, and the tabs are received in the annular spaces, respectively.

To enhance the driving connection between the driving device and the instrument, interlocking projections and recesses may be provided on the instrument and the driving device to provide a positive driving relationship between these components. Preferably, some of these projections and recesses are on the peripheral surface of the drive wheel of the driving device. The projections on the instrument are preferably located proximally of the distal end of the instrument, and at least some of the projections are along a region of the instrument which is at the driving device when the distal end of the instrument is adjacent the opening of the catheter.

Many of the features of this invention are applicable to both everting and non-everting catheter systems. Thus, the controller may be coupled to the proximal end portion of a catheter which may be either everting or non-everting.

The invention, together with additional features and advantages thereof, may best be understood by reference to the following description taken in connection with the accompanying illustrative drawings.

BRIEF DESCRIPTION OF THE DRAWINGS

FIG. 1 is a plan view illustrating one form of catheter system constructed in accordance with the teachings of this invention with the everting element everted and the instrument extending from the everting element.

FIG. 1A is an enlarged, axial, fragmentary sectional view illustrating a distal region of the everting catheter of FIG. 1 with the everting element everted.

FIG. 2 is a perspective view with parts broken away of one form of controller constructed in accordance with the teachings of this invention.

FIG. 3 is a sectional view taken generally along line 3—3 of FIG. 2 and also illustrating a portion of the inner catheter.

FIGS. 4, 5 and 6 are enlarged sectional views taken generally along lines 4—4, 5—5 and 6—6, respectively, of FIG. 3. FIG. 6 illustrates in phantom lines the rotation of the rotatable section of the housing.

FIG. 7 is a plan view of a non-everting catheter system constructed in accordance with the teachings of this invention.

FIG. 8 is a fragmentary, plan view partially in section illustrating one way to provide a positive drive connection between the drive wheel and the instrument.

DESCRIPTION OF THE PREFERRED EMBODIMENT

FIG. 1 shows an everting catheter system 11 which is particularly adapted for accessing the fallopian tubes; however, it should be understood that the features of this invention are also applicable to catheter systems adapted for other purposes. The catheter system 11 generally comprises an outer catheter 13, and inner catheter 15, an everting element 17 (FIG. 1A) and an elongated instrument 19. The outer catheter 13 includes an elongated, flexible catheter body 21 and an outer catheter fitting 23 coupled to the proximal end of the catheter body 21. The outer catheter 13 has an outer catheter lumen 25 (FIG. 1A) which extends from a proximal opening 27, which is provided by the outer catheter fitting 23, to a distal opening 29 (FIG. 1A) which, in this embodiment, is at the distal end of the catheter body 21. Of course, the catheter body 21 may have multiple lumens, if desired, and the distal opening 29 need not be at the distal end of the catheter body.

The catheter body 21 has a distal end portion 31 which, in its unstressed condition, may be straight or of any other shape designed to best gain access to a desired region of the body. As shown in FIG. 1, the distal end portion 31 is curved and forms a portion of a circular arc in the unstressed condition, and this facilitates access to the ostia of the fallopian tubes. However, the shape of the distal end portion 31 forms no part of this invention, and the distal end portion is shown for convenience in FIG. 1A as linear.

The outer catheter 13 may be of conventional construction, and the catheter body 21 may be constructed of a flexible, biocompatible polymeric material. The outer catheter fitting 23 has an injection leg 33 through which an inflation media can be supplied to the outer catheter lumen 25 to control the inversion and eversion of the everting element 17 in a known manner.

The inner catheter 15 is extendible through the proximal opening 27 of the outer catheter 13 and is movable longitudinally in the outer catheter lumen 25. The inner catheter 15 also includes a catheter body 35 and an inner catheter fitting 37 coupled to the proximal end of the catheter body 35. The inner catheter 15 has an inner catheter lumen 39 (FIG. 1A) which extends between a proximal opening 41 (FIG. 3) provided by one leg of the inner catheter fitting 37 and a distal opening 43 (FIG. 1A) at the distal end 44 of the catheter body 35.

The catheter body 35 may be flexible or rigid depending upon the nature and purpose of the catheter system 11. However, in this embodiment, a distal region of the catheter body 35 is flexible such that the portion of the catheter body 35 that is within the distal end portion 31 in all positions of the inner catheter 15 relative to the outer catheter 13 is flexible.

The fitting 37 has an injection leg 45 which can be used, for example, for injecting irrigation fluid, a contrast dye or drugs into the inner catheter lumen 39. The leg 45 can also be used for aspiration, if desired.

The everting element 17 (FIG. 1A) is a thin, flexible membrane which is constructed of a suitable polymeric material. The everting element 17 is bonded as by an adhesive to the catheter body 21 of the outer catheter 13 closely adjacent the distal opening 29 and to a distal tip region of the catheter body 35 of the inner catheter 15 in accordance with known techniques. This forms a chamber 47 with the catheter body 21 of the outer catheter 13. Consequently, inflation media from the injection leg 33 acting in the chamber 47 can bring about inversion and eversion of the everting element 17. The everting element 17 has a distal end 49 which, in the everted position of FIG. 1A, is located distally of the distal opening 29. The everting element 17 forms an extension 50 of the inner catheter lumen 39.

The instrument 19 is elongated and flexible. The instrument 19 is introduced to the inner catheter lumen 39 through the proximal opening 41 and can be moved both proximally and distally relative to the inner catheter 15 independently of the inner catheter. The instrument 19 terminates distally in a distal end 51 (FIG. 1A). In this embodiment, the instrument 19 is an endoscope for examination of the fallopian tubes. However, the instrument may be virtually any elongated, flexible instrument for medical purposes, such as a guidewire or other instrument for either visualizing or carrying out a procedure on an interior region of the body of a patient.

The catheter system 11 as described to this point in the Description of the Preferred Embodiment may be conventional. However, the catheter system 11 departs from conventional systems in providing a controller 53 (FIG. 1) coupled to the inner catheter 15 for moving the inner catheter in the outer catheter lumen 25 and instrument 19 in the inner catheter lumen 39 relative to the inner catheter.

The controller 53 includes a supporting structure which, in this embodiment, is in the form of a housing 55 (FIG. 2). Although the housing 55 can be of different constructions, in this embodiment, it is constructed of a suitable hard polymeric material, and it has a passage 57 extending therethrough which is adapted to receive the instrument 19 (FIG. 3). As illustrated, the housing 55 includes a mounting section 59 adapted to be coupled to the inner catheter 15, a drive section or rotatable section 61 and an elongated handle or handle section 63 which is adapted to be manually grasped. The mounting section 59 includes a short, internally threaded tube having an inner conical projection 65, a head 67 integral with the tube and an annular groove 69 between the head and the tube.

The handle section 63 includes an elongated tube 71 and a tubular connector 73 which receives and is affixed to the proximal end of the tube 71. The connector 73 has an annular groove 75. The grooves 75 and 69 are received within openings in the drive section 61 to mount the drive section 61 and the handle section 63 for rotational movement about the axis of the passage 57 relative to the mounting section 59 as described more specifically below. The drive section 61 is located between the mounting section 59 and the handle section 63 and has an opening 77.

The controller 53 includes a driving device 79 for moving the instrument 19 longitudinally in the inner catheter lumen 39 relative to the inner catheter 15. Although the driving device 79 can take different forms, including various ratchet or shuttle devices, it preferably includes a movable endless member, such as a drive wheel 81 for contacting and driving the instrument 19 longitudinally. The driving device 79 in this embodiment also includes a secondary wheel 83 which is cooperable with the drive wheel 81 for moving the instrument 19 longitudinally.

The wheels 81 and 83 are rotatably mounted on the drive section 61, and for that purpose, the drive section has opposite side walls 85 (FIGS. 4–6) joined by end walls 87 (FIGS. 2 and 3) and a transverse wall 89 (FIGS. 4–6). Thus, the drive section 61 forms a container with the opening 77 being generally opposite the transverse wall 89. Although the drive section 61 can be a one-piece member, in this embodiment, it comprises two molded half sections 90 (FIGS. 5 and 6) suitably adhered together.

Although the wheels 81 and 83 can be rotatably mounted on the drive section 61 in different ways, in this embodiment, each of the wheels includes oppositely extending stub shafts 91 (FIG. 4) received in inwardly facing bearings 93 integrally formed on the side walls 85, respectively. This mounts the wheels 81 and 83 for rotation about parallel rotational axes which extend transverse to the axis of the passage 57.

Although the wheels 81 and 83 can be configured in different ways, in this embodiment, they are identical, and each of them is of one-piece integral construction and includes a central drive disc 95 having a peripheral surface 97 and outer discs 99 having gear teeth 101 on their peripheral surfaces. With the wheels 81 and 83 rotatably mounted within the drive section 61 of the housing 55, the peripheral surfaces 97 are in generally confronting relationship and adapted to receive the instrument 19 therebetween so that, upon rotation of the drive wheel 81, the instrument 19 can be moved longitudinally in the passage 57 of the housing. In addition, the gear teeth 101 of the drive wheel 81 drivingly engage the gear teeth 101 of the secondary wheel 83 so that there is a positive drive connection between these two wheels, and slippage between these wheels is, therefore, prevented. This makes the secondary wheel 83 a drive wheel and improves the frictional characteristics of the wheels 81 and 83 on the instrument 19. If desired, the controller 53 may be constructed so that the secondary wheel 83 can be directly manually driven.

The opening 77 exposes a region of a portion of the drive wheel 81, and such region is engageable by a thumb of an operator to impart manual driving force to the drive wheel 81. In the illustrated embodiment, the exposed portion includes a portion of the peripheral surface of the drive wheel 81, i.e., a portion of the peripheral surface 97 and a portion of the peripheral surface containing the gear teeth 101. The drive section 61 completely encloses the wheels 81 and 83, except for this exposed portion of the drive wheel 81 so that the driving motion of the driving device 79 is unlikely to be unintentionally impeded. The handle section 63 of the housing 55 extends proximally of the region of the drive wheel 81 which is exposed through the opening 77 to conveniently position the handle section for manual grasping of the controller 53 and the exposed region of the drive wheel for being manually driven by the thumb of the operator.

The wheels 81 and 83 can be constructed of various different hard and soft materials, and it is not necessary that they both be constructed of the same material. Although the wheels 81 and 83 may be constructed of a metal, they may also be constructed of soft material, such as a soft rubber or a relatively hard polymeric material, such as hard polyurethane. If desired, one or both of the wheels 81 and 83 may have an outer, relatively softer, jacket. In the illustrated embodiment, each of the wheels 81 and 83 is of one-piece integral construction and is constructed of a relatively hard polymeric material to provide a strong positive driving connection between the interengaging teeth 101.

To enable the wheels 81 and 83 to grip the instrument 19 with the desired degree of compressive force, the peripheral surfaces 97 of the wheels 81 and 83 each have a groove 103 arranged to confront the corresponding groove of the other wheel as shown in FIG. 4. These grooves 103 are sized and adapted to receive the instrument 19 with the desired amount of compressive force for driving the instrument 19 without damaging the instrument.

Although the controller 53 can be used with many different kinds of instruments, the instrument 19 is an endoscope of the type having a distal end portion 105 (FIG. 1) which contains relatively delicate optics and which is of smaller cross-sectional area than a region of the instrument located proximally of a location 107 (FIG. 1) on the instrument. The two grooves 103 are sized to slidably receive the distal end portion 105 containing the delicate optics without compressively loading the distal end portion. It is not until the location 107 of the instrument 19 is located at the grooves 103 that the grooves begin to compressively load the instrument to form a driving connection therewith. In this manner, the instrument 19 can be more quickly advanced through the controller 53 up to the location 107 without turning of the wheels 81 and 83 and without risking damage to the optics in the distal end portion 105.

In this embodiment, the housing 55 is constructed so that the drive section 61 and the handle section 63 are rotatable as a unit about the axis of the passage 57 relative to the mounting section 59. Although this can be accomplished in different ways, in one preferred form, it is accomplished by adhesively attaching the drive section 61 to the handle section. In the illustrated embodiment, the connector 73 has a head 109 (FIGS. 3 and 5) within the drive section 61. The head 109 has lateral edges 111 (FIG. 5) which engage the opposite side walls 85, respectively, of the drive section 61 to prevent rotation of the connector 73 and the entire handle section 63 about the axis of the passage 57 relative to the drive section 61. Thus, the drive section 61 and the handle section 63 are not relatively rotatable about the axis of the passage 57. However, the head 67 (FIGS. 3 and 6) of the mounting section 59 is circular as viewed in FIG. 6 and is of small enough diameter so that the side walls 85 do not impede relative rotation between the mounting section 59 and the drive section 61 about the axis of the passage 57. Also, the fit between the opening in the end wall 87 and the mounting section 59 is sufficiently loose so as to permit this rotation. This structure which couples the drive section 61 to the mounting section 59 for relative rotation may be considered to be a coupling.

Although the controller 53 can be coupled to the inner catheter 15 in various different ways, such as by constructing the housing 55 and the inner catheter fitting 37 of one-piece integral construction, in this embodiment, the housing 55 is a separate element, and the controller 53 is releasably coupled to the inner catheter 15. As shown in FIG. 3, the inner catheter fitting 37 has a leg 113 with external threads which is threaded into the mounting section 59. A seal 115 is compressively loaded between the distal end of the projection 65 and an adjacent region of the leg 113 to provide a seal between the fitting 37 and the controller 53. The seal 115 is compressed sufficiently to provide a seal around the instrument 19.

As shown in FIG. 4, there is a portion of the passage 57 which extends proximally of the wheels 81 and 83. This invention provides means for guiding the instrument 19 to the wheels 81 and 83 and into the grooves 103. Although this means may take different forms, in the illustrated embodiment, it includes a pair of tabs 117 (FIGS. 2–5) which extend distally into the drive section 61 and into annular spaces or recesses 119 (FIGS. 2 and 4), respectively, between the discs 95 and 99. In this embodiment, the alignment tabs 117 extend at least to a location at which the wheels 81 and 83 are tangent to each other as shown in FIG. 3. Consequently, the tabs 117 serve to guide the instrument 19 into the grooves 103 when the instrument is being initially threaded into the controller 53.

In use, the outer catheter 13 with the everting element 17 in the inverted position, i.e., entirely within the outer catheter lumen 25, is inserted into the body of the patient to the desired region. The instrument 19 is then inserted through the passage 57 and the grooves 103 of the controller and through the inner catheter fitting 37 into the inner catheter lumen 39. If the instrument 19 is of the type described above having the distal end portion 105 of reduced diameter, it may be slid through the grooves 103 without rotation of the wheels 81 and 83. However, when the location 107 reaches the wheels 81 and 83, the instrument 19 can be advanced or moved distally only by rotating the drive wheel 81. In this position, the instrument 19 is frictionally gripped between the drive wheel 81 and the secondary wheel 83 so that rotation of the drive wheel 81 moves the instrument 19 longitudinally.

When the everting element 17 is everted, it grips the instrument 19 and pulls it distally. However, when it is desired to move the instrument 19 relative to the everting element 17, the controller 53 can be used. Movement of the instrument 19 longitudinally and longitudinal movement of the inner catheter 15 can be easily accomplished in a one-handed operation. Thus, the physician merely grasps the handle section 63 with his thumb contacting the drive wheel 81 and, by so doing, his thumb can drive the drive wheel and instrument, and his hand can move the inner catheter. These movements of the instrument 19 can be coordinated with the eversion and inversion of the everting element 17 as desired.

The driving device 79, and in particular the wheels 81 and 83, grip the instrument 19. Accordingly, rotation of the handle section 63 and the drive section 61 of the housing 55 relative to the mounting section 59 as shown, for example, in phantom lines in FIG. 6 rotates the instrument relative to the inner catheter 15. This may be useful, for example, if the instrument 19 has an angled distal tip section.

FIG. 7 shows a catheter system 11a which is identical to the catheter system 11 in all respects not shown or described herein. Portions of the catheter system 11a corresponding to portions of the catheter system 11 are designated by corresponding reference numerals followed by the letter "a."

The catheter system 11a is identical to the catheter system 11, except that the catheter is of the non-everting type. Thus, the catheter system 11a has no everting element and may be considered as comprising only the inner catheter 15a and the controller 53a. Of course, in the embodiment of FIG. 7, the catheter 15a is not an inner catheter but rather the only catheter of the system. The controller 53a is identical to the controller 53 and controls the longitudinal and rotational position of the instrument 19a within the catheter 15a.

FIG. 8 shows a catheter system 11b which is identical to the catheter system 11 in all respects not shown or described herein. Portions of the catheter system 11b corresponding to portions of the catheter system 11 are designated by corresponding reference numerals followed by the letter "b."

The only difference between the catheter systems 11 and 11b is that the latter provides interlocking projections or gear teeth 131 and recesses 133 on the instrument 19b and the drive wheel 81b and the secondary wheel 83b. This provides a positive driving relationship between the driving device 79b and, in particular, the wheels 81b and 83b, and the instrument 19b. The teeth 131 and the recesses 133 of the wheels 81b and 83b are located on the peripheral surfaces 97b, and they cooperate with the teeth 131 and recesses 133 of the instrument 19b to form a gear drive between these members. The teeth 131 and the recesses 133 can be provided on the instrument 19b in any suitable manner, such as by encasing the basic instrument in a jacket containing the teeth and recesses. The teeth 131 and recesses 133 can also be incorporated into the catheter system 11a of FIG. 7.

If the teeth 131 and recesses 133 are utilized, they need not extend for the full length of the instrument 19b. With reference to FIGS. 1 and 1A, the teeth 131 and recesses 133 may be located proximally of the distal end 51 of the instrument 19b and along a length of the instrument which includes a region of the instrument which is at the driving device 79b when the distal end of the instrument is adjacent the distal opening 29. With this construction, the teeth 131 may be proximally of the location 107 (FIG. 1) on the instrument 19b and will not hamper sliding movement of the instrument through the controller 53b up to the location 107. However, the positive drive connection between the instrument and the wheels 81b and 83b is obtained where that driving connection is desirable. By providing the positive drive connection, slippage between the drive wheel 81b and the instrument 19b is eliminated, and the physician is assured of having precise control over the longitudinal movements of the instrument.

Although exemplary embodiments of the invention have been shown and described, many changes, modifications and substitutions may be made by one having ordinary skill in the art without necessarily departing from the spirit and scope of this invention.

We claim:

1. A controller for moving an elongated medical instrument in a catheter comprising:
    a housing having a passage extending therethrough which is adapted to receive an elongated medical instrument, said housing including a mounting section adapted to be coupled to a catheter, a drive section and an elongated handle section which is adapted to be manually grasped;
    a drive wheel and a secondary wheel, each of said wheels having a peripheral surface, said wheels being rotatably mounted on the drive section with the peripheral surfaces in generally confronting relationship and adapted to receive the instrument therebetween so that upon rotation of the drive wheel the instrument can be moved longitudinally in the passage;
    a manual drive for manually rotating the drive wheel;
    said peripheral surfaces of said drive and secondary wheels defining a groove for receiving the instrument; and
    each of said drive wheel and said secondary wheel having an annular peripheral recess and the controller includes first and second members received in the annular peripheral recesses, respectively.

2. A controller as defined in claim 1 including a plurality of spaced projections on the peripheral surface of the drive wheel.

3. A controller as defined in claim 1 wherein said drive section is intermediate the mounting section and the handle section.

4. A controller as defined in claim 1 wherein the first and second members include first and second spaced alignment tabs for guiding the instrument between said wheels.

5. A controller for moving an elongated medical instrument in a catheter comprising:
    a housing having a passage extending therethrough which is adapted to receive an elongated medical instrument, said housing including a mounting section adapted to be coupled to a catheter, a drive section and an elongated handle section which is adapted to be manually grasped;
    a drive wheel and a secondary wheel, each of said wheels having a peripheral surface, said wheels being rotatably mounted on the drive section with the peripheral surfaces in generally confronting relationship and adapted to receive the instrument therebetween so that upon rotation of the drive wheel the instrument can be moved longitudinally in the passage;

a manual drive for manually rotating the drive wheel;

at least one of said peripheral surfaces of said wheels having a groove for receiving the instrument;

said drive section of the housing having an opening which exposes a portion of the peripheral surface of the drive wheel and the manual drive includes said portion of the peripheral surface of the drive wheel; and said housing shielding the peripheral surface of the secondary wheel against contact with a user of the controller when the handle section is manually grasped.

6. A controller as defined in claim 5 wherein both said drive wheel and said secondary wheel define said groove, each of said drive wheel and said secondary wheel has an annular peripheral recess and the controller includes first and second members received in the annular peripheral recesses, respectively.

7. A catheter system comprising:

an elongated catheter having a lumen adapted to receive an instrument, an opening communicating with the lumen and a proximal end portion;

a controller;

said controller including a supporting structure coupled to the proximal end portion of the catheter and a driving device on the supporting structure for moving the instrument in the lumen, said driving device including a movable endless member for contacting and driving the instrument longitudinally in the lumen and a wheel engagable with the instrument and cooperable with the movable endless member for moving the instrument longitudinally in the catheter; and the controller including a coupling for rotatably coupling a first portion of the controller to a second portion of the controller such that rotation of the second portion of the controller relative to the first portion of the controller rotates the instrument in the lumen.

8. A system as defined in claim 7 wherein the movable endless member includes a drive wheel.

9. A system as defined in claim 7 wherein the moveable endless member has a region engageable by a thumb of an operator to impart a manual driving force to the movable endless member for moving the instrument longitudinally in the lumen.

10. A system as defined in claim 7 wherein the supporting structure includes a housing having a passage communicating with the lumen and adapted to receive the instrument, and the driving device is carried by the housing.

11. A system as defined in claim 10 wherein the passage in the housing has an axis, said portion of the controller includes a rotatable section of said housing rotatable generally about the axis of the passage, said driving device is carried by the rotatable section and is capable of gripping the instrument so that rotation of the rotatable section rotates the instrument relative to the inner catheter.

12. A system as defined in claim 10 wherein the movable endless member has a region engageable by a thumb of an operator to impart a manual driving force to the movable endless member for moving the instrument and a region of said housing extends proximally of said region of the movable endless member to form a handle adapted to be manually grasped.

13. A system as defined in claim 10 wherein at least a portion of the passage extends proximally of the driving device and the controller includes means in said passage for guiding the instrument from said portion of the passage to the driving device.

14. A system as defined in claim 7 wherein the movable endless member includes a drive wheel having a peripheral surface and a plurality of spaced projections on the peripheral surface of the drive wheel.

15. A catheter system as set forth in claim 7 wherein the elongated catheter is an inner catheter and the system includes an elongated outer catheter having an outer catheter lumen and an opening, the inner catheter is movable in the outer catheter lumen and an everting element is coupled to the outer catheter and the inner catheter whereby with movement of the inner catheter in the outer catheter lumen the everting element can be everted through the opening in the outer catheter.

16. A catheter system comprising:

an elongated instrument;

an elongated catheter having a lumen for receiving the instrument, an opening communicating with the lumen and a proximal end portion;

a controller;

said controller including a supporting structure coupled to the proximal end portion of the catheter and a driving device on the supporting structure for contacting and driving the instrument longitudinally in the lumen;

interlocking projections and recesses on the instrument and driving device to provide a positive driving relationship between the driving device and the instrument; and the elongated catheter is an inner catheter and the system includes an elongated outer catheter having an outer catheter lumen and an opening, the inner catheter is movable in the outer catheter lumen and an everting element is coupled to the outer catheter and the inner catheter whereby with movement of the inner catheter in the outer catheter lumen the everting element can be everted through the opening in the outer catheter.

17. A system as defined in claim 16 wherein the driving device includes a drive wheel having a peripheral surface and some of said projections and recesses are on said peripheral surface.

18. A system as defined in claim 16 wherein all the projections on said instrument are located proximally of the distal end of the instrument and along a length of the instrument which includes a region of the instrument which is at the driving device when the distal end of the instrument is adjacent the opening of the catheter.

19. A controller for moving an elongated medical instrument in a catheter comprising:

a housing having a passage extending therethrough which is adapted to receive an elongated medical instrument, said housing including a mounting section adapted to be coupled to a catheter, a drive section and an elongated handle section which is adapted to be manually grasped;

a drive wheel and a secondary wheel, each of said wheels having a peripheral surface, said wheels being rotatably mounted on the drive section with the peripheral surfaces in generally confronting relationship and adapted to receive the instrument therebetween so that upon rotation of the drive wheel the instrument can be moved longitudinally in the passage;

a manual drive for manually rotating the drive wheel; and the passage having an axis and the controller including a coupling for rotatably coupling the drive section to the mounting section for rotation generally about the axis of the passage.

20. A controller for moving an elongated medical instrument in a catheter comprising:

a housing having a passage extending therethrough which is adapted to receive an elongated medical instrument, said housing including a mounting section adapted to be coupled to a catheter, a drive section and an elongated handle section which is adapted to be manually grasped;

a drive wheel and a secondary wheel, each of said wheels having a peripheral surface, said wheels being rotatably mounted on the drive section with the peripheral surfaces in generally confronting relationship and adapted to receive the instrument therebetween so that upon rotation of the drive wheel the instrument can be moved longitudinally in the passage;

a manual drive for manually rotating the drive wheel;

at least a portion of the passage extends proximally of the drive wheel and the secondary wheel, the controller includes first and second spaced alignment tabs for guiding the instrument between said wheels; and said drive wheel and said secondary wheel define first and second annular spaces and the tabs are received in the annular spaces, respectively.

21. A controller for moving an elongated medical instrument in a catheter comprising:

a housing having a passage extending therethrough which is adapted to receive an elongated medical instrument, said housing including a mounting section adapted to be coupled to a catheter, a drive section and an elongated handle section which is adapted to be manually grasped;

a drive wheel and a secondary wheel, each of said wheels having a peripheral surface, said wheels being rotatably mounted on the drive section with the peripheral surfaces in generally confronting relationship and adapted to receive the instrument therebetween so that upon rotation of the drive wheel the instrument can be moved longitudinally in the passage;

a manual drive for manually rotating the drive wheel;

at least one of said peripheral surfaces of said wheels having a groove for receiving the instrument; and the passage having an axis and the controller includes a coupling for rotatably coupling the drive section to the mounting section for rotation generally about the axis of the passage.

22. A controller as defined in claim 21 including means for holding the drive section against rotation relative to the handle section.

23. A controller for moving an elongated medical instrument in a catheter comprising:

a housing having a passage extending therethrough which is adapted to receive an elongated medical instrument, said housing including a mounting section adapted to be coupled to a catheter, a drive section and an elongated handle section which is adapted to be manually grasped;

a drive wheel and a secondary wheel, each of said wheels having a peripheral surface, said wheels being rotatably mounted on the drive section with the peripheral surfaces in generally confronting relationship and adapted to receive the instrument therebetween so that upon rotation of the drive wheel the instrument can be moved longitudinally in the passage;

a manual drive for manually rotating the drive wheel;

at least one of said peripheral surfaces of said wheels having a groove for receiving the instrument;

at least a portion of the passage extending proximally of the drive wheel and the secondary wheel;

first and second spaced alignment tabs for guiding the instrument between said wheels; and said drive wheel and said secondary wheel defining first and second annular spaces and the tabs being received in the annular spaces, respectively.

24. An everting catheter system comprising:

an elongated outer catheter having an outer catheter lumen and an opening;

an elongated inner catheter movable in the outer catheter lumen and having an inner catheter lumen adapted to receive an elongated instrument, the inner catheter having a proximal end portion;

an everting element coupled to the outer catheter and the inner catheter whereby with movement of the inner catheter in the outer catheter lumen the everting element can be everted through the opening in the outer catheter;

a housing coupled to the proximal end portion of the inner catheter whereby the inner catheter can be moved in the outer catheter lumen by movement of the housing, said housing having a passage communicating with the inner catheter lumen;

a driving device carried by the housing for moving the instrument in the inner catheter lumen relative to the inner catheter; and the housing having an axis, said housing including a mounting section coupled to the proximal end portion of the inner catheter, a rotatable section and a coupling for coupling the rotatable section to the mounting section so that the rotatable section is rotatable generally about the axis of the passage, said driving device being carried by the rotatable section and being capable of gripping the instrument so that rotation of the rotatable section rotates the instrument relative to the inner catheter.

* * * * *

UNITED STATES PATENT AND TRADEMARK OFFICE
CERTIFICATE OF CORRECTION

PATENT NO. : 5,389,100
DATED : February 14, 1995
INVENTOR(S) : Steven R. Bacich

It is certified that error appears in the above-indentified patent and that said Letters Patent is hereby corrected as shown below:

Column 11, line 55 after "said" insert --second--

Signed and Sealed this

Twelfth Day of December, 1995

Attest:

BRUCE LEHMAN

*Attesting Officer*   *Commissioner of Patents and Trademarks*